(12) United States Patent
Taylor et al.

(10) Patent No.: US 10,993,829 B2
(45) Date of Patent: May 4, 2021

(54) THERMAL SYSTEM (71) Applicant: Stryker Corporation, Kalamazoo, MI (US)

(72) Inventors: Gregory S. Taylor, Kalamazoo, MI (US); Marko N. Kostic, Portage, MI (US); Marco Constant, Portage, MI (US); Christopher John Hopper, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 341 days.

(21) Appl. No.: 15/820,558

(22) Filed: Nov. 22, 2017

(65) Prior Publication Data

US 2018/0140459 A1 May 24, 2018

Related U.S. Application Data (60) Provisional application No. 62/425,813, filed on Nov. 23, 2016.

(51) Int. Cl.
*A61F 7/00* (2006.01)
*A61F 7/02* (2006.01)
(Continued)

(52) U.S. Cl.
CPC .......... *A61F 7/0085* (2013.01); *A61B 5/0036* (2018.08); *A61B 5/01* (2013.01);
(Continued)

(58) Field of Classification Search
CPC .. A61F 7/0085; A61F 7/02; A61F 2007/0096; A61F 2007/0093;
(Continued)

(56) References Cited

U.S. PATENT DOCUMENTS 6,231,594 B1 5/2001 Dae
6,572,638 B1 6/2003 Dae et al.
(Continued)

FOREIGN PATENT DOCUMENTS

CN 107981966 A 5/2018
CN 208582583 U 3/2019
(Continued)

OTHER PUBLICATIONS

Altrix Precision Temperature Management System Stryker Operations Manuel, Dec. 2016.
(Continued)

*Primary Examiner* — Daniel W Fowler
*Assistant Examiner* — Tigist S Demie
(74) *Attorney, Agent, or Firm* — Warner Norcross + Judd LLP (57) ABSTRACT A thermal control unit supplies temperature controlled fluid to one or more thermal pads used to control the temperature of a patient. The thermal control unit includes a fluid outlet, fluid inlet, heat exchanger, pump, and a controller. The controller receives first and second data from at least two different sources to determine if the patient is shivering or not. The two different sources may include a temperature sensor adapted to detect a temperature of the fluid, a temperature sensor adapted to detect a temperature of the patient, a tissue oxygenation sensor, a vibration/motion sensor, a thermal image sensor, an electromyograph, and/or other sensors. In some embodiments, the thermal control unit takes one or more automatic actions in response to detection of patient shivering.

17 Claims, 5 Drawing Sheets

(51) Int. Cl.
*A61B 5/11* (2006.01)
*A61B 5/145* (2006.01)
*A61B 5/0488* (2006.01)
*A61B 5/00* (2006.01)
*A61B 5/01* (2006.01)

(52) U.S. Cl.
CPC .......... *A61B 5/0488* (2013.01); *A61B 5/1101* (2013.01); *A61B 5/14542* (2013.01); *A61B 5/4836* (2013.01); *A61F 7/02* (2013.01); *A61F 2007/0054* (2013.01); *A61F 2007/0056* (2013.01); *A61F 2007/0093* (2013.01); *A61F 2007/0096* (2013.01); *A61F 2007/0244* (2013.01)

(58) Field of Classification Search
CPC ...... A61F 2007/0056; A61F 2007/0054; A61F 2007/0244; A61B 5/0488; A61B 5/4836; A61B 5/01; A61B 5/14542; A61B 5/1101
See application file for complete search history.

(56) References Cited

U.S. PATENT DOCUMENTS

| | | | |
|---|---|---|---|
| 6,582,457 B2 | 6/2003 | Dae et al. | |
| 6,702,839 B1 | 3/2004 | Dae et al. | |
| 6,830,581 B2 | 12/2004 | Magers | |
| 7,008,444 B2 | 3/2006 | Dae et al. | |
| 8,617,230 B2 | 12/2013 | Diller et al. | |
| 8,706,207 B2 | 4/2014 | Flint | |
| 9,339,412 B2 | 5/2016 | Diller et al. | |
| 9,375,142 B2 | 6/2016 | Schultz et al. | |
| 9,549,844 B2 | 1/2017 | Diller et al. | |
| 9,763,823 B2 | 9/2017 | Voorhees et al. | |
| 2004/0087606 A1 | 5/2004 | Voorhees et al. | |
| 2006/0136023 A1 | 6/2006 | Dobak, III | |
| 2006/0190062 A1 | 8/2006 | Worthen | |
| 2009/0131835 A1* | 5/2009 | Voorhees | A61B 5/6828 600/595 |
| 2010/0087900 A1* | 4/2010 | Flint | A61B 5/1101 607/104 |
| 2014/0135879 A1 | 5/2014 | Flint | |
| 2014/0222121 A1 | 8/2014 | Spence et al. | |
| 2016/0058613 A1 | 3/2016 | Palazzolo et al. | |
| 2017/0224528 A1* | 8/2017 | Berg | A61F 7/02 |
| 2017/0281054 A1* | 10/2017 | Stever | A61B 5/1117 |
| 2017/0348145 A1 | 12/2017 | Voorhees et al. | |
| 2018/0140459 A1 | 5/2018 | Taylor et al. | |

FOREIGN PATENT DOCUMENTS

| | | |
|---|---|---|
| EP | 0898473 B1 | 3/2004 |
| JP | 2006504805 A | 2/2006 |

OTHER PUBLICATIONS

Arctic Sun 5000 Service Manual by Medivance, Inc., 2010-2011.
Gaymar Medi-Therm III, Hyper/Hypothermia Machine Ref MTA7912 Service Manual, Nov. 2009.
"Shivering Management During Therapeutic Temperature Modulation: Nurses' Perspective", Critical Care Nurse, col. 32, No. 1, Feb. 2012.
Sorin Group, Heater-Cooling System 3T, Operating Instructions, 2015.

* cited by examiner

THERMAL SYSTEM

CROSS-REFERENCE TO RELATED APPLICATIONS

This application claims priority to U.S. provisional patent application Ser. No. 62/425,813 filed Nov. 23, 2016, by inventors Gregory S. Taylor et al. and entitled THERMAL SYSTEM, the complete disclosure of which is incorporated herein by reference.

BACKGROUND

The present disclosure relates to a thermal control system for controlling the temperature of circulating fluid that is delivered to one or more thermal pads positioned in contact with a patient.

Thermal control systems are known in the art for controlling the temperature of a patient by providing a thermal control unit that supplies temperature controlled fluid to one or more thermal pads positioned in contact with a patient. The thermal control unit includes one or more heat exchangers for controlling the temperature of the fluid and a pump that pumps the temperature controlled fluid to the pad(s). After passing through the pad(s), the fluid is returned to the thermal control unit where any necessary adjustments to the temperature of the returning fluid are made before being pumped back to the pad(s). In some instances, the temperature of the fluid is controlled to a static target temperature, while in other instances the temperature of the fluid is varied as necessary in order to automatically effectuate a target patient temperature. The thermal control unit can therefore be used to warm or cool a patient.

The pads are placed in close contact with the patient in order to facilitate heat exchange between the patient and the pad. In one common arrangement, three pads are applied to the patient: one applied around the patient's torso, one applied around the patient's right leg, and one applied around the patient's left leg.

SUMMARY

The present disclosure provides various improved aspects to a thermal control system, including the thermal control unit and the thermal pads. These improved aspects include better detection of patient shivering. Such shivering impedes the progress of the cooling of a patient, causes metabolic and hemodynamic stress to the patient, and may have other undesirable effects. In some embodiments, the present disclosure allows detection of patient shivering even in cases where shivering is difficult for a caregiver to identify visually. Other improved aspects of the thermal control system are also disclosed herein and described in more detail below.

According to one embodiment of the present disclosure, a thermal control unit for controlling a patient's temperature is provided. The thermal control unit includes a fluid outlet adapted to fluidly couple to a fluid supply line, a fluid inlet adapted to fluidly couple to a fluid return line, a heat exchanger, a pump, and a controller. The pump circulates fluid from the fluid inlet through the heat exchanger and to the fluid outlet. The controller receives first data from a first source and second data from a second source and uses both the first data and the second data to determine if the patient is shivering.

According to another embodiment, a thermal pad is provided for controlling a patient's temperature. The thermal pad comprises an interior layer, exterior layer, a fluid chamber, and first and second sensors. The interior layer is adapted to be placed in contact with the patient. The exterior layer faces away from the patient. The fluid chamber is defined between the interior layer and the exterior layer and adapted to circulate a temperature controlled fluid from a fluid inlet in fluid communication with the fluid chamber to a fluid outlet in fluid communication with the fluid chamber. The first sensor detects a first characteristic associated with patient shivering, and the second sensor detects a second characteristic associated with patient shivering.

According to still another embodiment, a thermal control unit for controlling a patient's temperature is provided. The thermal control unit includes a fluid outlet, a fluid inlet, a heat exchanger, a pump, a temperature sensor, a port, and a controller. The fluid outlet is adapted to fluidly couple to a fluid supply line. The fluid inlet is adapted to fluidly couple to a fluid return line. The pump circulates fluid from the fluid inlet through the heat exchanger and to the fluid outlet. The temperature sensor measures a temperature of the circulating fluid. The port is adapted to receive external data from an external sensor adapted to detect a patient characteristic. The controller is adapted to use both the measured temperature of the circulating fluid and the external data to determine if the patient is shivering.

According to other aspects, the first and second sources are selected from the following: a sensor adapted to detect vibrations; a tissue oxygenation sensor adapted to detect changes in oxygenation levels in the patient's blood; a temperature sensor adapted to detect a temperature of the circulating fluid; a temperature sensor adapted to detect a temperature of the patient; a thermal image sensor adapted to capture thermal images of the patient; and an electromyograph adapted to detect electrical activity in the patient's muscles.

In some embodiments, the controller analyzes temperature readings from the temperature sensor and identifies at least one of the following: if additional energy necessitated by the patient's shivering is being used by the thermal control unit to cool the patient, or if a rate of cooling of the patient changes due to the patient's shivering.

In some of the embodiments where a tissue oxygenation sensor is included, the tissue oxygenation sensor is coupled to a thermal pad. The thermal pad fluidly couples to the fluid supply and fluid return lines of the thermal control unit. The tissue oxygenation sensor senses oxygenation levels in a region of the patient's body adjacent to the thermal pad.

The thermal control unit is further adapted to take an action in response to a determination that the patient is shivering, in some embodiments. The action is configurable by a user of the thermal control unit. The action may include automatically warming a selected region of the patient's body while continuing to deliver circulating fluid to the fluid outlet at a temperature less than the patient's body temperature. Such warming is accomplished by providing electrical heat in the selected region, in at least some embodiments. Alternatively, or additionally, the automatic action may include adjusting a control signal sent to the heat exchanger in response to the determination that the patient is shivering, and/or notifying the user of the determination that the patient is shivering without adjusting the control signal sent to the heat exchanger.

The thermal control unit may include a first cooling mode and a second cooling mode selectable by a user of the thermal control unit. When included, the first cooling mode cools the patient in a first manner and the second cooling mode cools the patient in a second manner. The different cooling modes may refer to different rates at which the patient is cooled, different temperatures of the fluid used to cool the patient, different maximum permissible differences between the patient temperature and the fluid temperature, and/or differences between closed and open loop control of the patient's temperature. In some of the embodiments where the thermal control unit includes multiple cooling modes, the controller is configurable by a user to automatically take a first action in response to a determination that the patient is shivering while the thermal control unit is operating in the first cooling mode, and to automatically take a second action in response to a determination that the patient is shivering while the thermal control unit is operating in the second cooling mode. The first action includes adjusting a control signal sent to the heat exchanger in response to the determination that the patient is shivering. The second action includes notifying the user of the determination that the patient is shivering without adjusting the control signal sent to the heat exchanger.

In some embodiments, the thermal pad includes a plurality of tissue oxygenation sensors adapted to detect changes in oxygenation levels in the patient's blood at multiple locations on the patient.

One or more electrodes are included in some embodiments of the thermal pad. The electrodes are coupled to the interior layer and adapted to detect electrical activity due to movement of the patient's muscles.

In some embodiments, the thermal control unit includes two or more ports for receiving data from two or more sensors that are external to the thermal control unit. The data received from the two or more ports is used to determine if the patient is shivering. The controller, in some embodiments, is adapted to analyze data from at least one of the ports with respect to the temperature of the circulating fluid to determine if changes in a cooling rate of the patient have occurred that are not caused by changes in the temperature of the circulating fluid.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
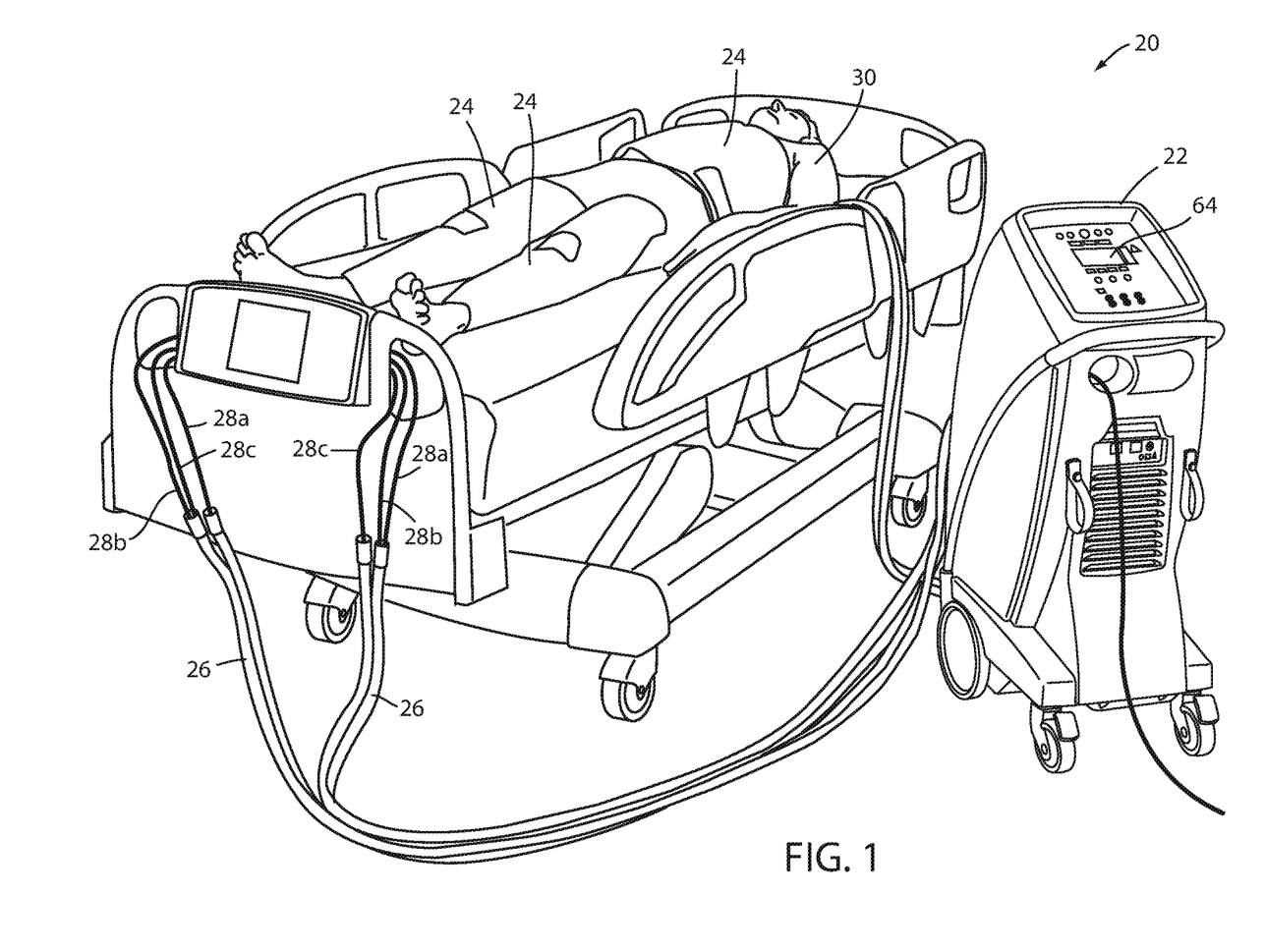
FIG. 1 is a perspective view of a thermal control system according to one aspect of the present disclosure shown applied to a patient on a patient support apparatus.

A thermal control system 20 according to one embodiment of the present disclosure is shown in FIG. 1. Thermal control system 20 is adapted to control the temperature of a patient 30, which may involve raising, lowering, or maintaining the patient's temperature, or combinations thereof. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, or other structure. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, etc.).

Thermal control unit 22 is coupled to thermal pads 24 via a plurality of hoses 26. Each hose includes one or more lines 28. In the embodiment shown in FIG. 1, each hose 26 includes a fluid supply line 28a, a fluid return line 28b, and one or more auxiliary lines 28c. Thermal control unit 22 delivers temperature controlled fluid (such as, but not limited to, water) to the thermal pads 24 via the fluid supply lines 28a. After the temperature controlled fluid has passed through thermal pads 24, thermal control unit 22 receives the temperature controlled fluid back from thermal pads 24 via the return lines 28b. Auxiliary lines 28c are used by thermal control unit 22 in different manners, depending upon the capabilities of thermal control unit 22, the construction of one or more of the thermal pads 24, and/or the desired treatment to be applied to the patient 30. As will be discussed in greater detail below, in some instances thermal control unit 22 uses an auxiliary line 28c to take one or more tissue oxygenation readings from a location of thermal pad 24 that is in contact with the patient's skin. In other instances, thermal control unit 22 uses an auxiliary line 28c to control one or more electric heaters that are incorporated into thermal pad 24. In still other instances, thermal control unit 22 uses auxiliary lines 28c to both take sensor readings (such as tissue oxygenation readings) and control one or more components of thermal pad 24 (such as an electric heater). Still other uses are discussed below.

In the embodiment of thermal control system 20 shown in FIG. 1, three thermal pads 24 are used in the treatment of patient 30. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply lines 28a, the temperature of the patient 30 can be controlled via the close contact of the pads 24 with the patient 30 and the resultant heat transfer therebetween.

Figure 2:
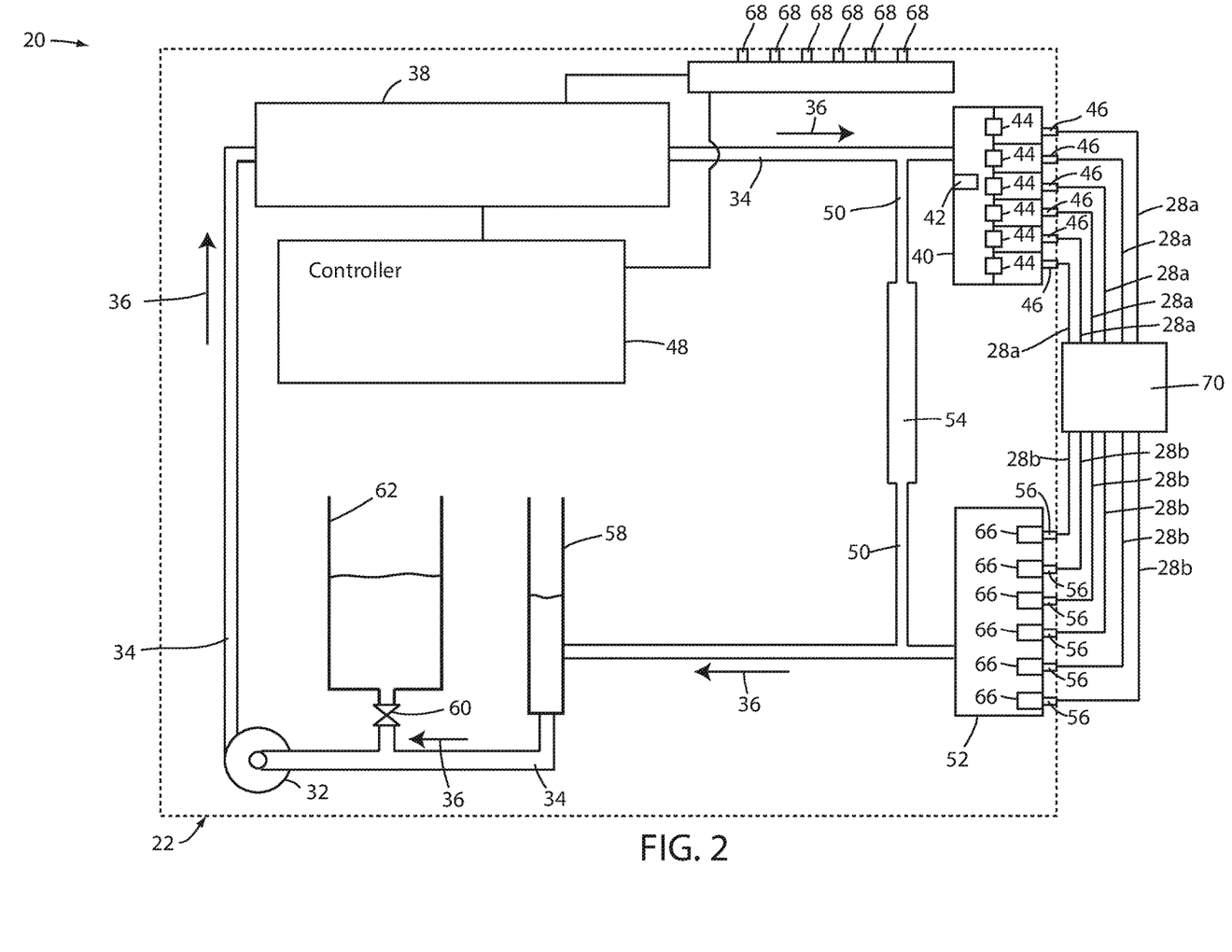
FIG. 2 is a block diagram of a control system for the thermal control unit of FIG. 1.

Thermal control unit 22 is adapted to raise or lower the temperature of the fluid supplied to thermal pads 24 via supply lines 28a. As shown in FIG. 2, thermal control unit 22 includes a pump 32 for circulating fluid through a circulation channel 34. Pump 32, when activated, circulates the fluid through circulation channel 34 in the direction of arrows 36 (clockwise in FIG. 2). Starting at pump 32 the circulating fluid first passes through a heat exchanger 38 where it is delivered to an outlet manifold 40 having an outlet temperature sensor 42, a plurality of valves 44, and a plurality of outlet ports 46. Although FIG. 2 illustrates six such outlet ports 46, it will be understood that this number may vary.

Temperature sensor 42 is adapted to detect a temperature of the fluid inside of outlet manifold 40 and report it to a controller 48. Valves 44 are adapted to move between open and closed positions (and in some embodiments, one or more positions therebetween) under the control of controller 48. Outlet ports 46 are adapted to be coupled to supply lines 28a of thermal control system 20 and deliver temperature controlled fluid thereto. Valves 44 control how much fluid flows from outlet manifold 40 to each of the supply lines 28a, as will be discussed in greater detail below. Supply lines 28a are, in turn, coupled to a thermal load 70. Thermal load 70 includes one or more thermal pads 24 that are used to control the temperature of a patient 30.

Control unit 22 also includes a bypass line 50 fluidly coupled to outlet manifold 40 and an inlet manifold 52. Bypass line 50 allows fluid to circulate through circulation channel 34 even in the absence of any thermal pads 24 or lines 28a being coupled to any of outlet ports 46. In the illustrated embodiment, bypass line 50 includes an optional filter 54 that is adapted to filter the circulating fluid. If included, filter 54 may be a particle filter adapted to filter out particles within the circulating fluid that exceed a size threshold, or filter 54 may be a biological filter adapted to purify or sanitize the circulating fluid, or it may be a combination of both. In some embodiments, filter 54 is constructed and/or positioned within thermal control unit 22 in any of the manners disclosed in commonly assigned U.S. patent application Ser. No. 62/404,676 filed Oct. 11, 2016, by inventors Marko Kostic et al. and entitled THERMAL CONTROL SYSTEM, the complete disclosure of which is incorporated herein by reference.

Inlet manifold 52 includes a plurality of inlet ports 56 (the precise number may vary from the six illustrated in FIG. 2) that receive fluid returning from the one or more connected thermal pads 24. The incoming fluid from inlet ports 56, as well as the fluid passing through bypass line 50, travels back toward the pump 32 into an air separator 58. Air separator 58 includes any structure in which the flow of fluid slows down sufficiently to allow air bubbles contained within the circulating fluid to float upwardly and escape to the ambient surrounding. In some embodiments, air separator 58 is constructed in accordance with any of the configurations disclosed in commonly assigned U.S. patent application Ser. No. 62/361,124 filed Jul. 12, 2016, by inventor Gregory S. Taylor and entitled THERMAL CONTROL SYSTEM, the complete disclosure of which is hereby incorporated herein by reference. After passing through air separator 58, the circulating fluid flows past a valve 60 positioned beneath a fluid reservoir 62 that supplies fluid to thermal control unit 22. After passing by valve 60, the circulating fluid travels to pump 32 and the circuit is repeated.

Controller 48 of thermal control unit 22 is contained within a main body of thermal control unit 22 and is in electrical communication with a variety of different sensors and/or actuators. More specifically, controller 48 is in electrical communication with pump 32, heat exchanger 38, a control panel 64 (FIG. 1), outlet temperature sensor 42, valves 44, a plurality of inlet temperature sensors 66, and a plurality of control ports 68.

Inlet temperature sensors 66 are positioned inside of inlet manifold 52 and measure the temperature of the fluid returning through each of inlet ports 56. That is, each temperature sensor 66 measures the temperature of fluid entering one of the inlet ports 56. One or more of the inlet ports 56, in turn, are coupled to return lines 28b that return fluid from thermal load 70 to thermal control unit 22.

Control panel 64 allows a user to operate thermal control unit 22, including setting a desired fluid target temperature and/or a desired patient target temperature, and/or to control other aspects of thermal control unit 22. Control panel 64 communicates with controller 48 and includes controls enabling a user to turn control unit 22 on and off, as well as one or more controls enabling the user to select a target temperature for the fluid delivered to thermal pads 24. In some embodiments, control panel 64 also allows a user to select from different modes for controlling the patient's temperature. One of the modes includes a manual mode in which the user selects a target temperature for the fluid. Control unit 22 then makes adjustments to heat exchanger 38 in order to ensure that the temperature of the fluid exiting supply lines 28a is at the user-selected temperature.

Another one of the modes is an automatic mode. When the user selects the automatic mode, the user selects a target patient temperature, rather than a target fluid temperature. After selecting the target patient temperature, controller 48 makes automatic adjustments to the temperature of the fluid in order to bring the patient's temperature to the desired patient target temperature. In this mode, the temperature of the circulating fluid may vary as necessary in order to bring about the target patient temperature. Both the manual and automatic modes can be used for cooling and heating the patient.

In some embodiments, when the user selects the automatic mode, the thermal control unit 22 is configured to allow the user to select one or more desired heating or cooling rates for use in the automatic mode. When such rates are selected by the user, thermal control unit 22 not only brings the patient to the target patient temperature, but does so at the rate specified by the user. Still other variables, such as the maximum difference between the patient's temperature and the fluid temperature, may also be selected by the user using control panel 64, in at least some embodiments. In addition, control panel 64 allows a user to configure how thermal control unit 22 controls the thermal pads in light of the detection of shivering by the patient, as will be discussed more below.

Both the outlet temperature sensor 42 and one or more of the inlet temperature sensors 66 may be used to provide feedback to controller 48, depending upon the embodiment of thermal control unit 22, so that controller 48 can adjust heat exchanger 38, as appropriate, in order to effectuate closed-loop control of the temperature of the circulating fluid.

Each control port 68 couples to an auxiliary line 28c. Auxiliary lines 28c may be coupled to one or more sensors and/or one or more electric heating elements, as will be discussed below. Such sensors include, but are not limited to, a tissue oxygenation sensor, a temperature sensor, a vibration or motion detector, and/or one or more other sensors.

Controller 48 includes any and all electrical circuitry and components necessary to carry out the functions and algorithms described herein, as would be known to one of ordinary skill in the art. Generally speaking, controller 48 may include one or more microcontrollers, microprocessors, and/or other programmable electronics that are programmed to carry out the functions described herein. It will be understood that controller 48 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-485, universal serial bus (USB), etc.

Controller 48 uses the outputs of outlet temperature sensor 42 and the outputs from one or more of the inlet temperature sensors 66 and/or one or more sensors (which are communicated via auxiliary lines 28c and control ports 68) to control heat exchanger 38 and/or pump 32. Controller 48 controls the heat exchanger and/or pump 32 such that the temperature of the circulating fluid has its temperature adjusted (or maintained) in accordance with the operating mode (manual or automatic) selected by the user of thermal control unit 22. Controller 48 may control the temperature of the fluid using a closed-loop proportional-integral (PI) controller, a closed-loop proportional-integral-derivative (PID), controller, or some other type of closed-loop controller.

Control unit 22 may also be modified to include one or more flow sensors that measure the rate of fluid flow and report this information to controller 48. In such modified embodiments, controller 48 uses the flow rate in determining what control signals to send to heat exchanger 38, valves 44, pump 32, and/or one or more thermal pads via control ports 68.

It will be understood by those skilled in the art that the particular order of the components along circulation channel 34 of control unit 22 may be varied from what is shown in FIG. 2. For example, although FIG. 2 depicts pump 32 as being upstream of heat exchanger 38 and air separator 58 as being downstream of heat exchanger 38, this order may be changed. Air separator 58, pump 32, heat exchanger 38 and reservoir 62 may be positioned at any suitable location along circulation channel 34. Indeed, in some embodiments, reservoir 62 is moved so as to be in line with and part of circulation channel 34, rather than external to circulation channel 34 as shown in FIG. 2, thereby forcing the circulating fluid to flow through reservoir 62 rather than around reservoir 62.

Further details regarding the construction and operation of one embodiment of thermal control unit 22 that are not described herein are found in commonly assigned U.S. patent application Ser. No. 14/282,383 filed May 20, 2014, by inventors Christopher Hopper et al. and entitled THERMAL CONTROL SYSTEM, the complete disclosure of which is incorporated herein by reference.

Figure 3:
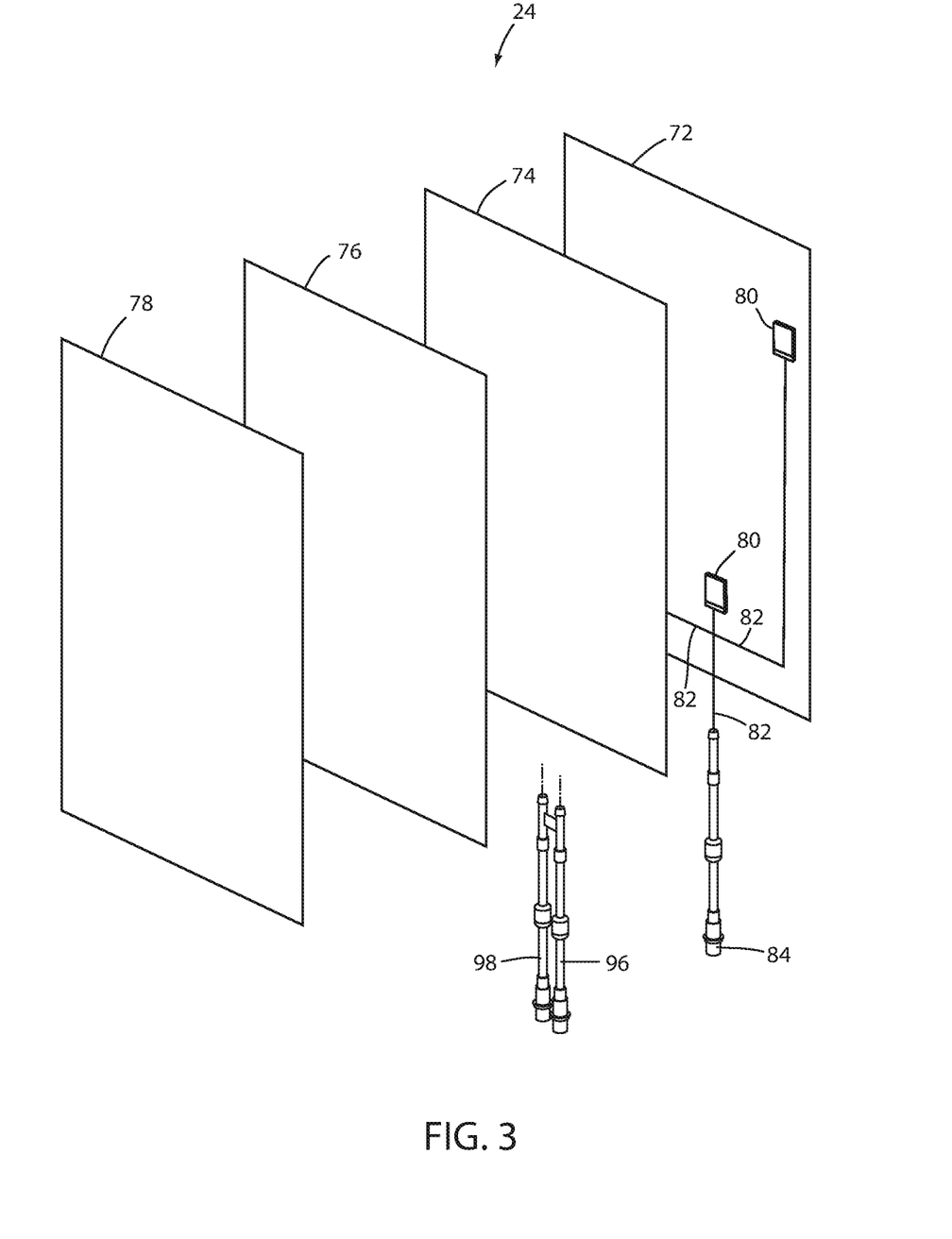
FIG. 3 is an exploded perspective view of one of the thermal pads of the thermal control system of FIG. 1.

FIG. 3 illustrates in greater detail one embodiment of a thermal pad 24 that may be used with the thermal control system 20 of FIG. 1. Thermal pad 24 includes a sensor layer 72, a lower chamber layer 74, an upper chamber layer 76, and an insulating layer 78. Sensor layer 72 includes one or more sensors 80 and is adapted to be placed in contact with the skin of a patient whose temperature is to be controlled. The specific type(s) and number of sensors 80 incorporated into sensor layer 72 may vary from embodiment to embodiment. In some embodiments, sensor layer 72 includes at least one sensor 80 that is a tissue oxygenation sensor adapted to detect changes in the amount of oxygen in the patient's tissue adjacent the sensor 80. Although different types of tissue oxygenation sensors may be used, one suitable type is disclosed in commonly assigned U.S. patent application Ser. No. 14/884,222 filed Oct. 15, 2015, by inventors Marko Kostic et al. and entitled SYSTEMS AND METHODS FOR DETECTING PULSE WAVE VELOCITY, the complete disclosure of which is incorporated herein by reference. Another suitable oxygenation sensor is disclosed in commonly assigned U.S. patent application Ser. No. 15/200,818 filed Jul. 1, 2016, by inventors Marko Kostic et al. and entitled SYSTEMS AND METHODS FOR STROKE DETECTION, the complete disclosure of which is also incorporated herein by reference. Still other types of tissue oxygenation sensors may also be used. Further, in some embodiments, multiple tissue oxygenation sensors 80 are included in sensor layer 72.

Sensor layer 72 may also or alternatively include one or more sensors 80 adapted to detect vibrations and/or other types of movement of the patient due to shivering of the patient (FIG. 3). Such sensors 80 include, but are not limited to, accelerometers, piezoelectric sensors (including, but not limited to, piezo polymer films), piezoresistive sensors, or other type of vibration/motion sensors. In some embodiments, as will be discussed more below, sensor layer 72 includes both one or more tissue oxygenation sensors 80 and one or more vibration sensors 80. In some embodiments, sensor layer 72 includes one or more sensors 80 that are able to detect breathing of the patient due to the patient's movement. The breathing signals are analyzed by the control unit and may be used as evidence of patient shivering (e.g. increases in the patient's breathing rate due to shivering).

Sensor layer 72 may also or alternatively include one or more temperature sensors 80 for detecting a temperature of the patient at the location(s) where the temperature sensors 80 contacts the patient's skin. The use of such temperature sensors 80 may be in addition to, or in lieu of, a conventional patient temperature probe that is adapted to measure a core temperature of the patient and which, in some embodiments, is plugged into thermal control unit 22 and reports its temperature readings to thermal control unit 22.

Sensor layer 72 may also or alternatively include electromyograph (EMG) electrodes 80 adapted to detect a surface EMG. Such electrodes 80 detect the electrical activity of the muscles within the vicinity of the electrodes. In some embodiments, more than two EMG electrodes 80 are included in one or more arrays that are adapted to detect any patient shivering within the entire region, or a substantial portion of the region, where thermal pad 24 contacts the patient. In still other embodiments, sensor layer 72 may include one or more ports, or other structures, for coupling to one or more needle electrodes used to detect an intramuscular EMG.

Regardless of the specific types of sensor(s) 80 included within sensor layer 72, each sensor 80 is electrically coupled via one or more electrical lines 82 to an auxiliary port 84.

Auxiliary port 84 is adapted to electrically couple to an auxiliary line 28c. In this manner, the outputs of each sensor 80 are electrically fed to auxiliary port 84 and an auxiliary line 28c. The auxiliary line 28c carries the sensor outputs from thermal pad 24 to thermal control unit 22. Thermal control unit 22 processes and uses the outputs of sensors 80 in one or more manners, as will be discussed in greater detail below.

In some embodiments, sensor layer 72 is comprised of, or has attached to it, a gel layer that is adapted to releasably adhere to the skin of the patient and thereby maintain contact with the patient's skin during the course of thermal therapy. The particular gel material used may vary. In some embodiments, the gel is a urethane gel. The specific chemical composition of the urethane gel can be adjusted to change the adhesive properties of the side of layer 72 that contacts the patient's skin. When sensor layer 72 includes gel, it may be secured to lower chamber layer 74 by RF welding, lamination, by being poured thereon, or by other means. Regardless of the specific gel used and the specific manner it is secured to lower chamber layer 74, the gel should provide suitable adhesion to the surface of the patient's skin in order to resist physical separation between the pad 24 and the patient, yet not be so resistant to physical separation so as to cause discomfort to the patient when the pad 24 is subsequently removed.

Lower chamber layer 74 is designed to face toward the patient 30 while upper chamber layer 76 is designed to face away from the patient 30 (FIG. 3). Lower chamber layer 74 and upper chamber layer 76 are bonded to each other around their perimeters. In some embodiments, sensor layer 72 and insulation layer 78 are also bonded about their peripheries (and/or at internal locations within their peripheries) to lower and upper chamber layers 74 and 76, respectively. Insulating layer 78 provides thermal insulation to thermal pad and may be bonded to upper chamber layer 76 over substantially the entire exterior surface of upper chamber layer 76. Lower chamber layer 74 and upper chamber layer 76 may be constructed from any suitable plastic material that is flexible enough to conform to the patient's body and that provides good thermal conductivity. In some embodiments, lower chamber layer 74 and upper chamber layer 76 are constructed from a polyester and/or nylon composite. Other materials, however, may be used. Insulation layer 78 is constructed from any suitably flexible material that has relatively poor thermal conductivity properties so as to thermally insulate the other layers (and the fluid contained therein) from the temperature of the ambient surroundings. In some embodiments, insulation layer 78 is constructed from material that includes a polyester foam, or other type of foam. Still other constructions are possible.

Figure 4:
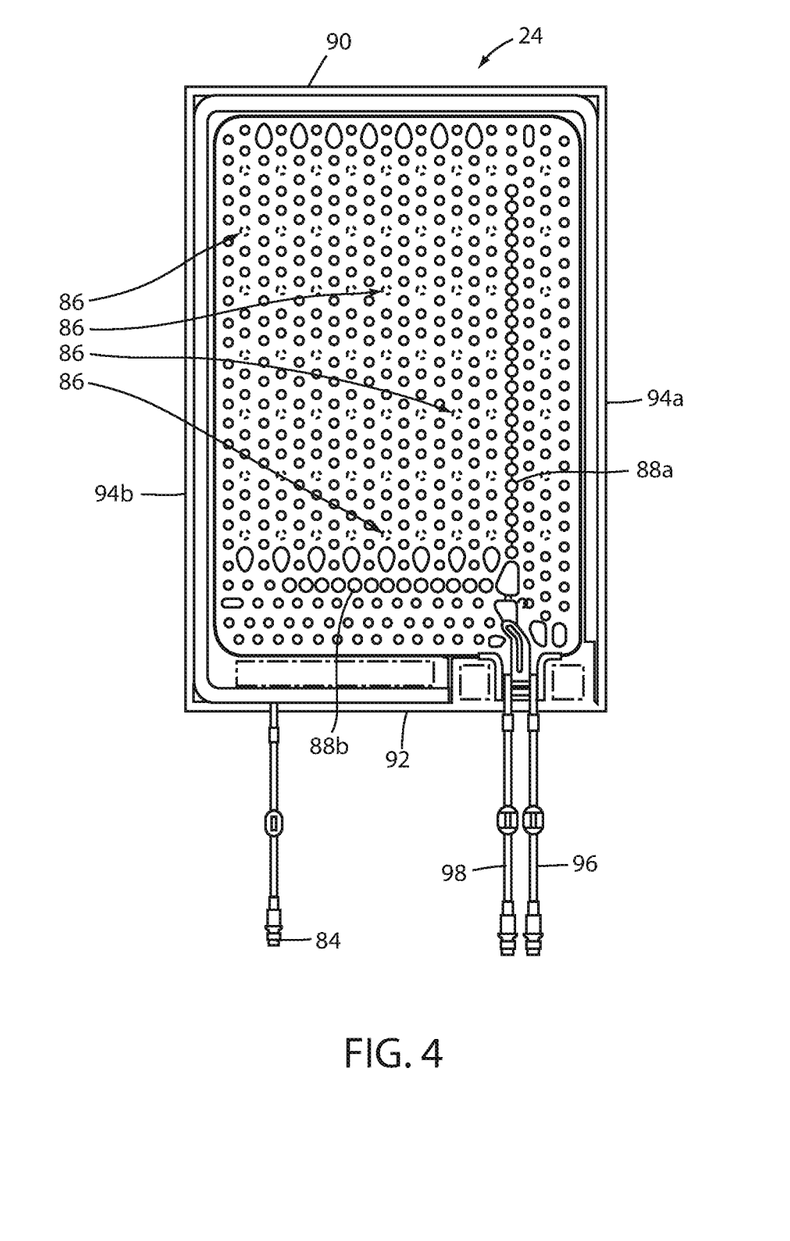
FIG. 4 is a plan view of the thermal pad of FIG. 2.

The bonding of lower chamber layer 74 and upper chamber layer 76 to each other about their periphery may be accomplished in any suitable manner. In some embodiments, the bonding is carried out using welds. Such welds may be implemented via heat welding, ultrasonic welding, Radio Frequency (RF) welding, or by other types of welding. In addition to being bonded to each other around their perimeters, lower chamber layer 74 and upper chamber layer 76 are bonded to each other at a plurality of internal locations 86 (FIG. 4). The space between lower chamber layer 74 and upper chamber layer 76 where they are not bonded to each other defines a fluid chamber in which the temperature controlled fluid supplied by thermal control unit 22 (via supply line 28a) circulates.

In some regions of thermal pad 24, bonding locations 86 are contiguous with each other to create one or more fluid channel walls 88 within thermal pad 24 (FIG. 4). One such wall 88a extends contiguously for a majority of the height of thermal pad 24 (e.g. in a direction from a top 90 to bottom 92), while another such wall 88b extends for a majority of the width of thermal pad 24 (e.g. in a direction from a first side 94a to a second side 94b). In some embodiments, one or more walls 88 may be included that divide thermal pad 24 into one or more fluidly isolated zones, such as disclosed in commonly assigned U.S. patent application Ser. No. 62/373,564 filed Aug. 11, 2016, by inventors James Galer et al. and entitled THERMAL SYSTEM, the complete disclosure of which is incorporated herein by reference.

In general, thermal pad 24 includes one or more walls 88—arranged in any suitable layout—that define one or more fluid channels within thermal pad 24. Temperature controlled fluid supplied to thermal pad 24 via inlet line 96 (which couples to a fluid supply line 28a of thermal control unit 22) flows into thermal pad 24, through the one or more channels, and exits thermal pad 24 via an outlet line 98 (which is coupled to a fluid return line 28b of thermal control unit 22). Temperature controlled fluid is therefore circulated throughout the interior of thermal pad 24 and then returned to thermal control unit 22.

In some embodiments, thermal pad 24 may also include additional layers beyond those shown in FIG. 3. When such additional layers are included, multiple chambers may be defined within a thermal pad 24. Examples of such multi-chamber thermal pads 24 are disclosed in commonly assigned U.S. patent application Ser. No. 62/373,658 filed Aug. 11, 2016, by inventors James Galer et al. and entitled THERMAL THERAPY DEVICES, the complete disclosure of which is incorporated herein.

Although not shown, thermal pad 24 may also include one or more straps that are used to secure thermal pad 24 to patient 30 when in use. Each strap may be adapted to releasably attach to another strap after thermal pad 24 has been wrapped around the patient 30. In some embodiments, the straps include hook and loop type fasteners, such as those sold under the tradename Velcro, while in other embodiments, the straps include one or more repositionable tapes. In other embodiments, the straps include other types of fasteners for securing themselves to each other in order to maintain pad 24 in a wrapped stated around the patient's leg or torso.

Although thermal pad 24 of FIGS. 3 & 4 is shown as having a generally rectangular shape, it will be understood by those skilled in the art that this may be varied greatly. That is, thermal pad 24 may take on any shape that is conducive to being wrapped around one or more portions of patient 30. In some embodiments, those thermal pads 24 that are intended to be wrapped around the patient's torso have a different shape than those intended to be wrapped around the patient's legs. Those adapted to be wrapped around the patient's legs may include one or more cutouts or contours that allow the patient to bend his or her knees while thermal pads 24 are wrapped around his or her legs.

Controller 48 of thermal control unit 22 is adapted to automatically detect if a patient undergoing thermal treatment is shivering or not. Controller 48 determines if the patient is shivering or not based on two or more sources of information. The specific sources vary in different embodiments. In a first embodiment which will be discussed extensively below, one of the sources includes one or more accelerometers 80 (or one or more other types of motion/vibration sensors 80) from sensing layer 72, and another one of the sources includes one or more temperature sensors.

Other combinations of sources, however, may be used, as will be discussed later within this document.

In the illustrated embodiment, one or more of the temperature sensors are internal to thermal control unit 22, such as temperature sensors 42 and 66. These temperature sensors detect the amount of heat removed from the patient by determining the difference between the temperature of the fluid delivered to thermal pad 24 and the temperature of the fluid returned from thermal pad 24 to thermal control unit 22. As will be discussed in greater detail below, controller 48 compares the rate of heat removal from the patient with the rate at which the temperature of the patient is decreasing and looks for changes in the relationship between these two rates that signify the likelihood of shivering.

Although other configurations are possible, and some of these are discussed in greater detail below, for purposes of the immediately following written description, thermal control unit 22 will be described as using motion/vibration sensors 80 as the first source of information for determining if a patient is shivering and using the combination of internal temperature sensors 42, 66 and an external patient temperature sensor as the second source of information for determining if a patient is shivering. In this set of embodiments, controller 48 is configured to analyze data from both of these sources and use the resulting analysis to determine if the patient is shivering or not.

In one such embodiment, controller 48 separately analyzes the data from each source, compares the analyzed data from each source to a corresponding shivering criterion, and if the analyzed data from either source meets its corresponding shivering criterion, controller 48 determines that the patient is shivering. If neither criterion is met, controller 48 then compares each set of analyzed data to a second corresponding shivering criterion that is less stringent than the first shivering criterion. If both of the second shivering criteria are met, controller 48 determines that shivering is taking place. If only one of the second shivering criteria is met, controller 48 concludes that shivering is not taking place. Fresh data from each source is gathered repetitively and re-analyzed throughout the thermal treatment process so that thermal control unit 22 is able to detect the occurrence of shivering at any time during the thermal treatment. This process is described in more detail below with respect to motion/vibration sensors 80 and the temperature sensors.

Controller 48 repetitively receives data from the motion/vibration sensors 80 within each thermal pad 24. Controller 48 compares this data to a first shivering criterion, which contains first and second thresholds for the magnitude of the motion/vibration and/or frequency of the motion/vibration, respectively. Thus, if the motion/vibration sensor 80 detects movement and/or vibrations that exceed both the amplitude threshold and the frequency threshold, controller 48 concludes that the patient is shivering. As will be discussed in greater detail below, controller 48 may automatically take one or more steps in response to this determination of shivering.

If the outputs from the motion/vibration sensor 80 do not meet both the amplitude and frequency thresholds, controller 48 analyzes the outputs from the temperature sensors 42, 66. When analyzing the outputs from temperature sensors 42, 66, controller 48 is configured to calculate the rate of heat loss of the patient. This can be calculated in a variety of different manners. In one manner, controller 48 determines the difference between the temperature of the fluid exiting thermal control unit 22 via temperature sensor 42 and the temperature of the fluid returning from an individual thermal pad 24, as detected by the temperature sensor 66 corresponding to that individual thermal pad 24. If the fluid is not being circulated at a constant rate, controller 48 uses one or more flow sensors to multiply the temperature difference by the flow rate in order to determine an estimate of the effective rate at which heat is being withdrawn from the patient is obtained (this ignores any heating of the fluid due to the ambient air and/or other non-patient sources, which are presumed to occur at a substantially constant rate, and thus immaterial to this calculation). Multiplying the temperature difference by the flow rate can determine the "effective" heat transfer rate (i.e. when not considering specific heat and density of the circulating fluid). As known, the average heat transfer rate can be calculated at any instant according to the formula below:

$$h = (q)(c_p)(\rho)(dt)$$

where h equals the heat flow rate, q equals the volumetric flow rate of the circulating fluid, $c_p$ equals the specific heat capacity of the circulating fluid, $\rho$ equals the density of the circulating fluid, and dt equals the temperature difference between the fluid supplied to thermal pad 24 and the fluid returned from thermal pad 24.

The term "effective heat transfer rate" is used here to signify that, in at least some embodiments, a numerical value indicative of the rate of heat transfer can be determined without using and/or knowing the specific heat and/or density of the circulating fluid. By looking for changes in the relationship between this numerical value and the rate at which the patient's temperature is changing, patient shivering can be detected. Stated alternatively, it is possible to simplify the aforementioned equation by calculating the product of the volumetric flow rate and the temperature difference and comparing changes in that product with changes in the temperature of the patient. If the product increases (indicative of more heat being removed from the patient) without a corresponding decrease in the temperature of the patient, it is presumed that the extra heat being removed from the patient is coming from an increase in the rate at which the patient is generating heat due to shivering. In other embodiments, controller 48 may be programmed to use the specific heat value and/or density of the circulating fluid to determine an actual amount of heat that is being removed from the patient.

In addition to determining the rate at which heat is being withdrawn from the patient, controller 48 also examines the rate at which the patient's temperature is falling. This is determined using either a conventional patient temperature probe that is coupled to a selected location of the patient's body and that communicates via a cable with thermal control unit 22, or via one or more patient temperature sensors 80 that are integrated into thermal pads 24. Controller 48 compares the rate at which the patient's temperature is falling to the rate at which heat is being removed from the patient and looks for one or both of the following: increases in the heat removal rate that are not accompanied by a corresponding expected decrease in the patient's temperature, and/or decreases in the rate at which the patient is being cooled that are not accompanied by corresponding decreases in the rate at which heat is being removed from the patient. Either or both of these conditions results from a patient's shivering because the shivering results in more heat being generated by the patient's body, thereby requiring more heat to be removed from the body to cool it a given amount than would otherwise be required if the patient were not shivering. In other words, if the patient's temperature tends to drop 0.2 degrees Celsius after removing X kilocalories when the patient is not shivering, it will take the removal of Y kilocalories to drop the patient's temperature 0.2 degrees Celsius when the patient is shivering, where Y is greater than X.

Figure 5:
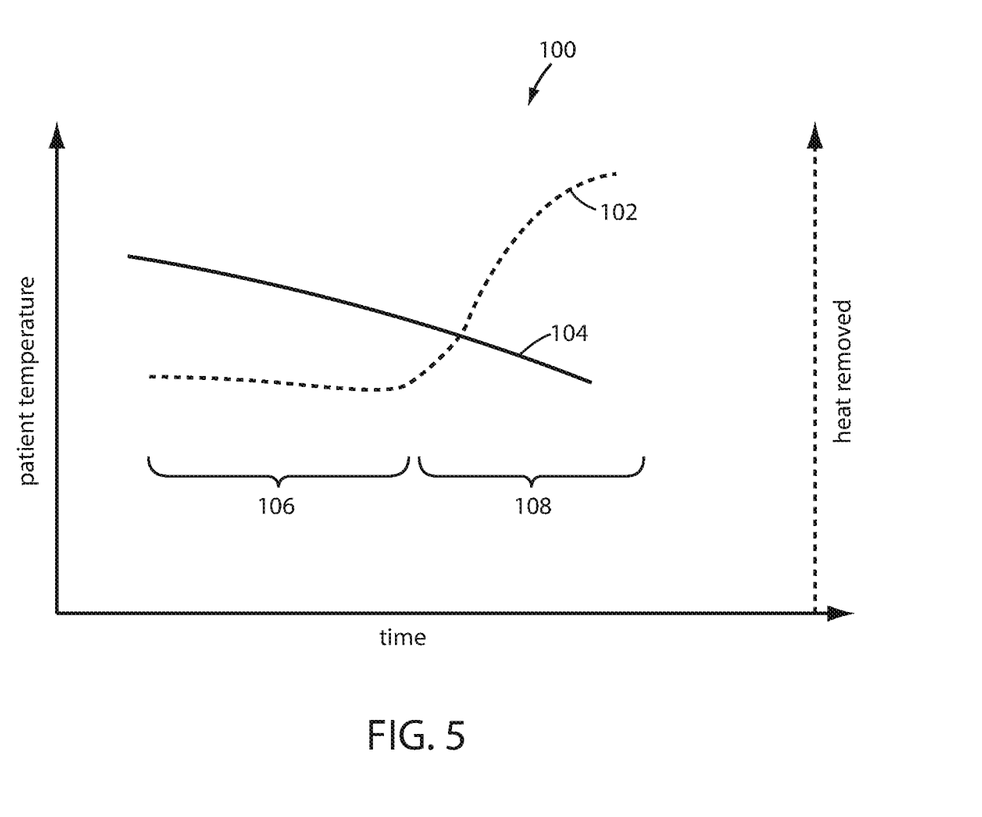
FIG. 5 is an illustrative graph of a patient's temperature and heat outflow over time illustrating one manner of detecting patient shivering.

An illustrative example of one possible relationship between the rate at which heat is removed from a patient and the rate at which the patient's temperature is dropping is shown in FIG. 5. FIG. 5 shows a graph 100 that plots an amount of heat 102 removed from a patient over time by thermal pads 24. Graph 100 also plots the patient's temperature 104 over time. As can be seen, the patient temperature tends to drop at a relatively steady rate for an initial time period 106 during which heat is being removed from the patient at a substantially constant rate. During a subsequent time period 108, however, the rate at which heat is removed from the patient jumps upwardly without any appreciable increase in the rate at which the patient's temperature is dropping. This means that the patient is generating more heat than during initial period 106. The added heat generation is most likely due to the patient starting to shiver. Controller 48 therefore examines the patient temperature data and the heat removal data and looks for moments when the substantially linear relationship between these two variables changes. Such a change is indicative of patient shivering.

As was noted previously, controller 48 is programmed in at least one embodiment to use the two data sources both individually and collectively. When using the two sources individually, controller 48 concludes that shivering is occurring if either source meets a corresponding criterion. When using the two sources collectively, controller 48 concludes that shivering is occurring only if both sources meet corresponding criteria. Using the above-described embodiment as an example in which controller 48 uses vibration/motions sensors 80 as a first data source and heat flow and temperature data as a second source, controller 48 compares the outputs of the vibration/motion sensor 80 to a first threshold. If the vibration/motion sensor 80 is detecting more movement and/or vibrations than this threshold, then controller 48 concludes the patient is shivering, regardless of what the second source of data is indicating. Controller 48 also examines the patient temperature and heat flow data and looks for changes in the substantially linear relationship between the patient cooling rate and heat removal rates, as described above. If it detects a change that is greater than a second threshold, it concludes that the patient is shivering regardless of what the first source of data (motion/vibration sensors 80) is indicating.

If neither the first nor second source of data is individually indicating that the patient is shivering, then controller 48 uses the data from these two sources collectively. In one embodiment, it does this by comparing the first source of data to a third threshold and the second source of data to a fourth threshold wherein the third threshold is less stringent than the first threshold, and the fourth threshold is less stringent than the second threshold. If the first source of data exceeds the third threshold and the second source of data exceeds the fourth threshold, then controller 48 concludes that the patient is shivering. On the other hand, if controller 48 determines that the first source of data has exceeded the third threshold but that the second source of data has not exceeded the fourth threshold, or vice versa, controller 48 concludes that shivering is not taking place.

The combined individual and collective analyses of the data from multiple data sources is, as mentioned previously, only one manner in which controller 48 may be configured to process the data from multiple sources. For example, in another embodiment, controller 48 is configured to only collectively process the data from the multiple sources and does not ever determine that a patient is shivering based on data from only a single source. Still other manners of processing the data from multiple sources may also be used.

Controller 48 performs the analysis of the data from multiple sources for each of the thermal pads 24 that are attached to patient 30. Thus, controller 48 evaluates the vibration/motion sensor(s) 80 associated with each of the pads 24, both individually and collectively with respect to the patient temperature data and cooling rate data. If controller 48 detects that shivering is occurring based on the data from any one of the multiple thermal pads 24, then controller 48 concludes that the patient is shivering.

Controller 48 is configured to take one or more steps automatically in response to the detection of patient shivering. In some embodiments, the specific steps automatically taken are configurable by the user of thermal control unit 22. Further, in some embodiments, the specific steps taken automatically depend upon what mode the thermal control unit is operating in (e.g. automatic mode versus manual mode). In most embodiments, the automatic steps taken include, at a minimum, notification to the user that shivering has been detected. This is notification may be carried out both locally and remotely. Local notification includes aural and/or visual notifications that are generated by, or on (e.g. on control panel 64), thermal control unit 22. Remote notifications include messages sent by thermal control unit 22 to a remote device, such as a local area network having a conventional mobile communications server that forwards received messages to the mobile electronic devices (e.g. smart phones) of designated hospital personnel, such as the caregivers overseeing, or participating in, the thermal treatment of the patient.

In some embodiments, in addition to automatically notifying one or more individuals of the detection of patient shivering, controller 48 is configured to automatically make changes to the thermal treatment being applied to the patient. For example, if thermal control unit 22 is operating in the automatic mode wherein it is attempting to control the patient's temperature to a target patient temperature, controller 48 may automatically reduce the rate at which the patient's temperature is being moved toward the target temperature. Indeed, in some embodiments, thermal control unit 22 may be programmed to terminate cooling of the patient when shivering is detected. Thermal control unit 22 is also configurable in some embodiments to automatically start warming of the patient when shivering is detected and terminate the warming when the shivering has ceased. When operating in the manual mode, if thermal control unit 22 detects patient shivering, it may not take any different action with respect to the control signals provided to heat exchanger 38, thereby leaving the cooling process unchanged. Alerting the user of the shivering, however, may be automatically performed. Other manners of automatically responding to shivering when operating in the manual mode can be selected by the user.

In at least one embodiment, thermal control unit 22 is configurable to automatically apply heat to one or more areas of the patient's body that are rich in thermoregulatory receptors in response to the detection of patient shivering. This application of heat is done while the patient continues to have his or her core body temperature reduced via thermal pads 24. For example, in at least one embodiment, an electric heating unit is included within the thermal pad 24 that heats a selected area of the patient's body that is rich in thermoreceptors. The heating of this area is done with the intent of fooling the patient's thermoregulatory system into reacting as if the patient were sufficiently warm when, in fact, the patient is being cooled. One such location is the area between the patient's shoulder blades and the lower neck region of the patient.

In some embodiments of thermal pads 24, one or more electrical heating elements are included in locations that will be placed in contact with thermoreceptor rich areas of the patient's body. The electrical heating elements are coupled to an auxiliary line 28c that feeds into thermal control unit 22. Thermal control unit 22 uses the auxiliary line 28c to control the heating element. Thus, if thermal control unit 22 detects shivering, it is configurable to automatically being applying heat to one or more of the electric heaters until the shivering stops. This automatic step is taken in addition to the notification step mentioned above. Further, this automatic heating step take place while cooling fluid is still being circulated through the chambers of thermal pads 24. The patient therefore continues to be cooled while heat is selectively applied in one or more specific locations of the patient's body where thermoreceptors are highly concentrated. In those embodiments of thermal pads 24 where an electrical heating element is included, the electrical heating element may be positioned at a location where the circulating fluid of the pad 24 does not circulate so that the heat from the electric heater does not directly heat the circulating fluid.

In some embodiments, other types of heat sources besides electrical heaters may be used with the thermal pads 24 for this selective application of heat. For example, in some embodiments, thermal pads 24 include separate zones wherein at least one of the zones is positioned to contact an area of the patient's body that has a high concentration of thermoreceptors. If and when thermal control unit 22 detects a patient shivering, thermal control unit 22 is configurable to control the fluid in that zone differently from the fluid flowing outside of that zone. Such different control may include sending fluid to that zone that has a different temperature (e.g. warmer fluid). Alternatively, or additionally, such different control may include changing a valve configuration that controls the flow of fluid to that zone. The changing valve may include shutting off fluid completely to that zone, reducing the flow of fluid, and/or diverting fluid at a different temperature to that zone. Suitable thermal pads 24 having individually controllable zones for this type of control are disclosed in commonly assigned U.S. patent application Ser. No. 62/373,564 filed Aug. 11, 2016, which has already been incorporated herein by reference.

In addition to, or in lieu of, the two data sources discussed above (motion/vibration sensors 80 and the heat removal rate of the patient relative to the rate of patient temperature change, as sensed by temperature sensors 42, 66 and one or more patient temperature probes), thermal control unit 22 is configured in some embodiments to utilize one or more other sources of information for determining if a patient is shivering or not. These other sources of data include, but are not limited to, the following: one or more tissue oxygenation sensors, one or more EMG electrodes, one or more thermal cameras, one or more force sensors built into a patient support apparatus (e.g. load cells of a hospital bed or stretcher), and/or one or more optical and/or laser sensors. These sources may be used in any combination with each other and/or in any combination with the two sources discussed above. Thermal control unit 22 can therefore take on a wide variety of different configurations, depending upon which specific sources of shivering information are being provided to it.

When one or more tissue oxygenation sensors are coupled to the patient at one or more locations, their outputs are forwarded to thermal control unit 22 via one or more auxiliary lines 28c. Thermal control unit 22 receives the outputs from the tissue oxygenation sensors and looks for increases in the tissue oxygenation levels. Such increases are a sign of shivering. If the increases meet one or more thresholds (which may include an individual threshold and a collective threshold, as discussed above), thermal control unit 22 concludes that the patient is shivering.

When one or more EMG electrodes are coupled to thermal control unit 22, their outputs are forwarded to thermal control unit 22 via one or more auxiliary lines 28c. Thermal control unit 22 receives the outputs from the EMG electrodes and looks for increases in the muscle activity of the patient, as indicated by increased electrical potentials sensed by the EMG electrodes. Such increases are a sign of shivering. If the increases meet one or more thresholds (which may include an individual threshold and a collective threshold, as discussed above), thermal control unit 22 concludes that the patient is shivering.

When one or more thermal image sensors are coupled to thermal control unit 22, their outputs are forwarded to thermal control unit 22 via one or more auxiliary lines 28c coupled to ports 68, or via another connection to thermal control unit 22. Thermal control unit 22 processes the thermal images to determine temperatures associated with the regions of the patient's body covered by the thermal pads 24. In some embodiments, thermal control unit 22 processes the thermal images to determine temperatures associated with other regions of the patient's body. Regardless of the specific regions monitored by thermal control unit 22, controller 48 processes the thermal images to look for temperatures that don't decrease as quickly as expected (given the heat being removed from the patient's body via the temperature controlled fluid pumped to pads 24), or that remain stable despite the thermal cooling of the pads 24, or in some cases, increase slightly despite the thermal cooling of the pads 24. These are indicators that the patient has started shivering. If any of these conditions meet one or more thresholds (which may include individual threshold and collective thresholds, as discussed above), thermal control unit 22 concludes that the patient is shivering. In at least one embodiment, thermal control unit 22 is coupled to thermal image sensors of the type disclosed in commonly assigned U.S. patent application Ser. No. 14/692,871 filed Apr. 22, 2015, by inventors Marko Kostic et al. and entitled PERSON SUPPORT APPARATUS WITH POSITION MONITORING, the complete disclosure of which is incorporated herein by reference.

In those embodiments of thermal control unit 22 where controller 48 is configured to detect shivering based upon the rate at which the patient's temperature is falling, controller 48 may be modified to examine the temperature of the fluid being delivered to the patient without estimating the quantity of heat being removed from the patient. For example, if thermal control unit 22 is operating in an automatic mode and has been instructed by a user to cool the patient at a particular rate, controller 48 monitors the temperature of the fluid delivered to the thermal pads 24 and looks for drops in this temperature from a baseline level. Such drops are indicative of thermal control unit 22 having to work harder to maintain the target rate at which the patient is cooled, and such additional work is likely due to the patient having started to shiver. Controller 48 therefore examines data from outlet temperatures sensor 42 to detect if any such drops have occurred for each of the thermal pads 24 that are coupled to thermal control unit 22.

Although the thermal control systems described herein have been primarily disclosed to detect shivering by examining at least two different sources of shivering information, it will be understood that in at least some embodiments, thermal control system 20 may be modified to detect shivering using only a single source of shivering information. For example, in at least one embodiment, thermal control unit 22 detects shivering by looking at the outputs from one or more tissue oxygenation sensors. In another embodiment, thermal control unit 22 detects shivering by only using patient temperature data and heat flow data (i.e. by comparing the rate of heat removal from the patient to the rate at which the patient's temperature is decreasing). In still other embodiments, only one or more EMG sensors are used to detect patient shivering.

In addition to any of the aforementioned modifications, it will also be understood that the shivering detection techniques disclosed herein can be applied to thermal control systems that control a patient's temperature using one or more catheters, either in addition to, or in lieu of, the thermal pads 24.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit for controlling a patient's temperature, the thermal control unit comprising:
   a fluid outlet adapted to fluidly couple to a fluid supply line;
   a fluid inlet adapted to fluidly couple to a fluid return line;
   a heat exchanger;
   a pump for circulating fluid from the fluid inlet through the heat exchanger and to the fluid outlet; and
   a controller adapted to receive first data from a first source and second data from a second source, the controller further adapted to use both the first data and the second data to determine if the patient is shivering, the controller further adapted to perform the following
   (a) notify a user that the patient is shivering if the first data exceeds a first threshold but the second data does not exceed a second threshold;
   (b) notify the user that the patient is shivering if the second data exceeds the second threshold but the first data does not exceed the first threshold;
   (c) notify the user that the patient is shivering if the first data does not exceed the first threshold but does exceed a third threshold and the second data does not exceed the second threshold but does exceed a fourth threshold, wherein the third threshold is less stringent than the first threshold and the fourth threshold is less stringent than the second threshold; and
   (d) not notify the user that the patient is shivering if either the first data does not exceed the third threshold or the second data does not exceed the fourth threshold.

2. The thermal control unit of claim 1 wherein the first source is a sensor adapted to detect vibrations.

3. The thermal control unit of claim 2 wherein the second source includes at least one of the following: a tissue oxygenation sensor adapted to detect changes in oxygenation levels in the patient's tissue; a temperature sensor adapted to detect changes in a temperature of the circulating fluid; or a temperature sensor adapted to detect changes in a temperature of the patient.

4. The thermal control unit of claim 3 wherein the tissue oxygenation sensor is coupled to a thermal pad fluidly coupled to the fluid supply line and the fluid return line such that the tissue oxygenation sensor senses oxygenation levels in a region of the patient's body adjacent to the thermal pad.

5. The thermal control unit of claim 3 wherein the controller is further adapted to take an action in response to a determination that the patient is shivering, the action being configurable by the user of the thermal control unit, the action being different from notifying the user that the patient is shivering.

6. The thermal control unit of claim 5 wherein the action includes automatically warming a selected region of the patient's body while continuing to deliver circulating fluid to the fluid outlet at a temperature less than the patient's body temperature.

7. The thermal control unit of claim 3 wherein the thermal control unit includes a first cooling mode and a second cooling mode selectable by the user of the thermal control unit, the first cooling mode cooling the patient in a first manner and the second cooling mode cooling the patient in a second manner.

8. The thermal control unit of claim 7 wherein the controller is configurable by the user to automatically adjust a control signal sent to the heat exchanger in response to a determination that the patient is shivering while the thermal control unit is operating in the first cooling mode, and to automatically notify the user of the determination that the patient is shivering without adjusting the control signal sent to the heat exchanger in response to a determination that the patient is shivering while the thermal control unit is operating in the second cooling mode.

9. The thermal control unit of claim 2 wherein the second source includes a temperature sensor adapted to detect at least one of the following: changes in a temperature of the circulating fluid and changes in a temperature of the patient; and wherein the controller is adapted to analyze changes in temperature readings from the temperature sensor and identify at least one of the following: if additional energy necessitated by the patient's shivering is being used by the thermal control unit to cool the patient, or if a rate of cooling of the patient changes due to the patient's shivering.

10. The thermal control unit of claim 2 wherein the controller is further adapted to receive third data from a third source and also use the third data to determine if the patient is shivering.

11. The thermal control unit of claim 10 wherein the second source is a first temperature sensor adapted to detect changes in a temperature of the circulating fluid and the third source is a second temperature sensor adapted to detect changes in a temperature of the patient.

12. The thermal control unit of claim 1 wherein the first source is a first one of, and the second source is a second one of, the following group: a sensor adapted to detect vibrations; a tissue oxygenation sensor adapted to detect changes in oxygenation levels in the patient's blood; a temperature sensor adapted to detect temperature changes in the circulating fluid; a temperature sensor adapted to detect temperature changes in the patient; a thermal image sensor adapted to capture thermal images of the patient and detect temperature changes in the patient; and an electromyograph adapted to detect changes in electrical activity in the patient's muscles.

13. The thermal control unit of claim 1 wherein the controller is further adapted to take an action in response to a determination that the patient is shivering, the action being configurable by the user of the thermal control unit, the action being different from notifying the user that the patient is shivering.

14. The thermal control unit of claim 13 wherein the action includes automatically warming a selected region of the patient's body while continuing to deliver the circulating fluid to the fluid outlet at a temperature less than the patient's body temperature.

15. The thermal control unit of claim 1 wherein the thermal control unit includes a first cooling mode and a second cooling mode selectable by the user of the thermal control unit, the first cooling mode cooling the patient in a first manner and the second cooling mode cooling the patient in a second manner.

16. The thermal control unit of claim 15 wherein the controller is configurable by the user to automatically take a first action in response to a determination that the patient is shivering while the thermal control unit is operating in the first cooling mode, and to automatically take a second action in response to a determination that the patient is shivering while the thermal control unit is operating in the second cooling mode.

17. The thermal control unit of claim 16 wherein the first action includes adjusting a control signal sent to the heat exchanger in response to the determination that the patient is shivering, and the second action includes notifying the user of the determination that the patient is shivering without adjusting the control signal sent to the heat exchanger.

* * * * *